United States Patent [19]
Quinn et al.

[11] Patent Number: 5,542,846
[45] Date of Patent: Aug. 6, 1996

[54] DENTAL TOOL CHUCK

[75] Inventors: Michael J. Quinn, Grover; George E. Richmond, St. Louis, both of Mo.

[73] Assignee: Young Dental Manufacturing, Co., Inc., Earth City, Mo.

[21] Appl. No.: 315,963

[22] Filed: Sep. 30, 1994

[51] Int. Cl.⁶ ........................................ A61C 1/14
[52] U.S. Cl. .................. 433/127; 279/82; 279/106
[58] Field of Search ........................... 433/126, 127, 433/128, 129, 125, 147; 279/37, 74, 82, 106

[56] References Cited

U.S. PATENT DOCUMENTS

| | | | |
|---|---|---|---|
| 3,132,426 | 5/1964 | White | 433/132 |
| 3,156,963 | 11/1964 | Owen | 279/106 |
| 3,324,553 | 6/1967 | Borden | 433/126 |
| 3,637,050 | 1/1972 | Hoffmeister | 433/132 |
| 4,682,949 | 7/1987 | Warrin | 433/81 |
| 4,874,314 | 10/1989 | Fleer et al. | 433/129 |
| 5,040,980 | 8/1991 | Heil | 433/127 |
| 5,090,906 | 2/1992 | Pernot | 433/127 |
| 5,108,066 | 4/1992 | Lundstrom | 248/410 |
| 5,224,681 | 7/1993 | Lundstrom | 248/410 |

FOREIGN PATENT DOCUMENTS 664516 3/1988 Switzerland ................ 433/127

*Primary Examiner*—Stephen Funk
*Attorney, Agent, or Firm*—Polster, Lieder, Woodruff & Lucchesi

[57] ABSTRACT

A chuck mechanism for holding rotating tools in gear driven or turbine driven medical/dental devices. The chuck includes a bur tube which releasably receives a shaft of a dental tool, a tilt plate which extends through the bur tube and which has a hole through which the tool extends, and a tilt plate pusher which is moveable axially with respect to the bur tube. The tilt plate is moveable between a first, unlocked, position in which the edges of the tilt plate hole are spaced slightly from the dental tool shaft so that the shaft may be freely moved axially relative to the tilt plate, and a second, locked, position in which the tilt plate edges contact the shaft to prevent axial and rotational movement of the shaft relative to the tilt plate. The tilt plate is preferably spring biased to its locked position, and the tilt plate pusher is preferably operated by a push button to move the tilt plate to its open position. In another embodiment, the tilt plate is positively held in its locked position by a threaded piece.

38 Claims, 9 Drawing Sheets

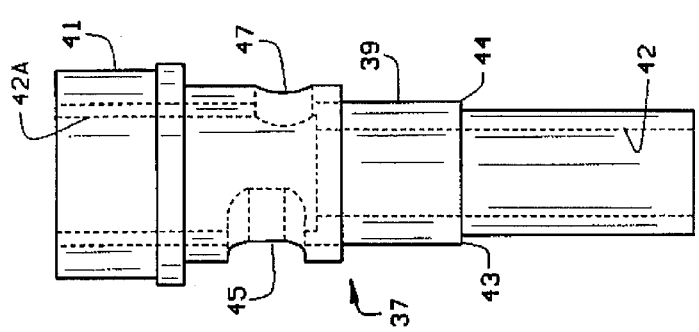
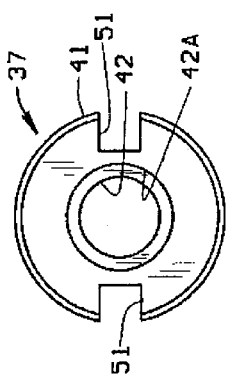
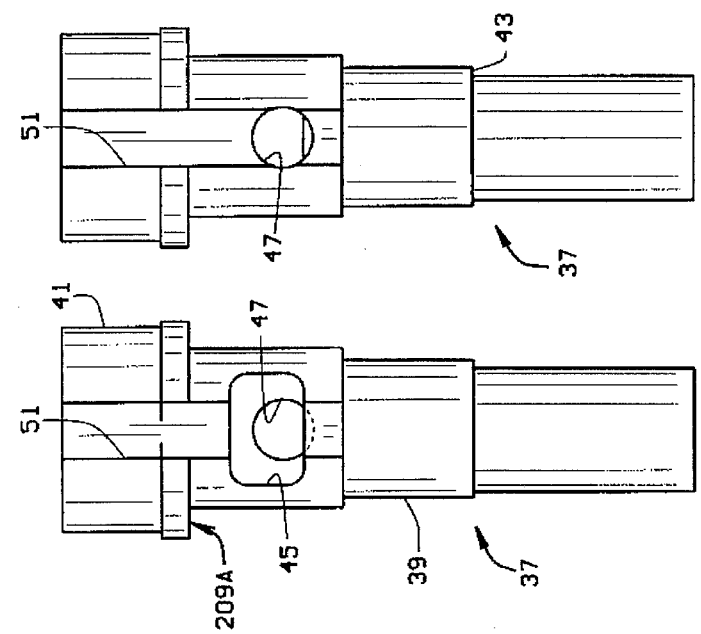
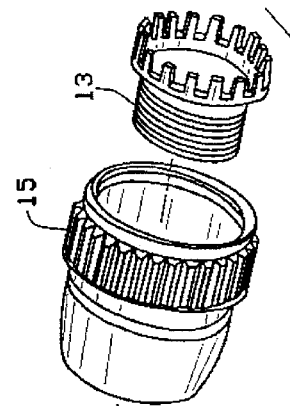
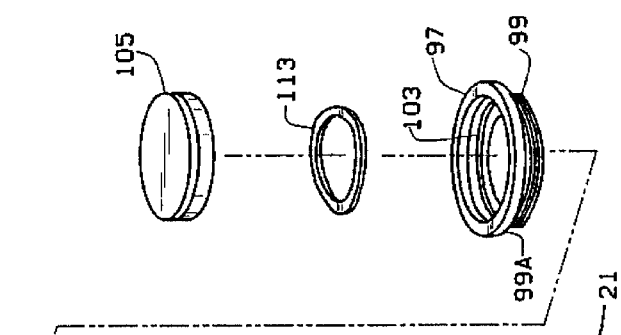
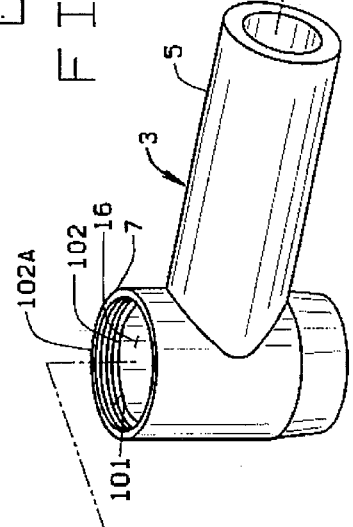
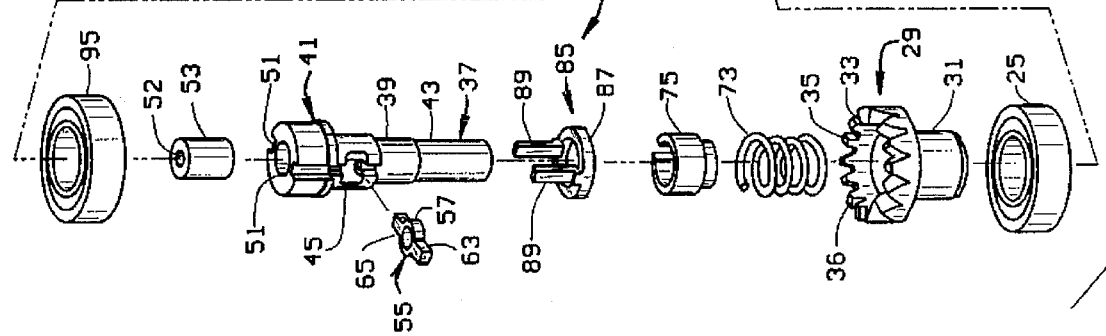

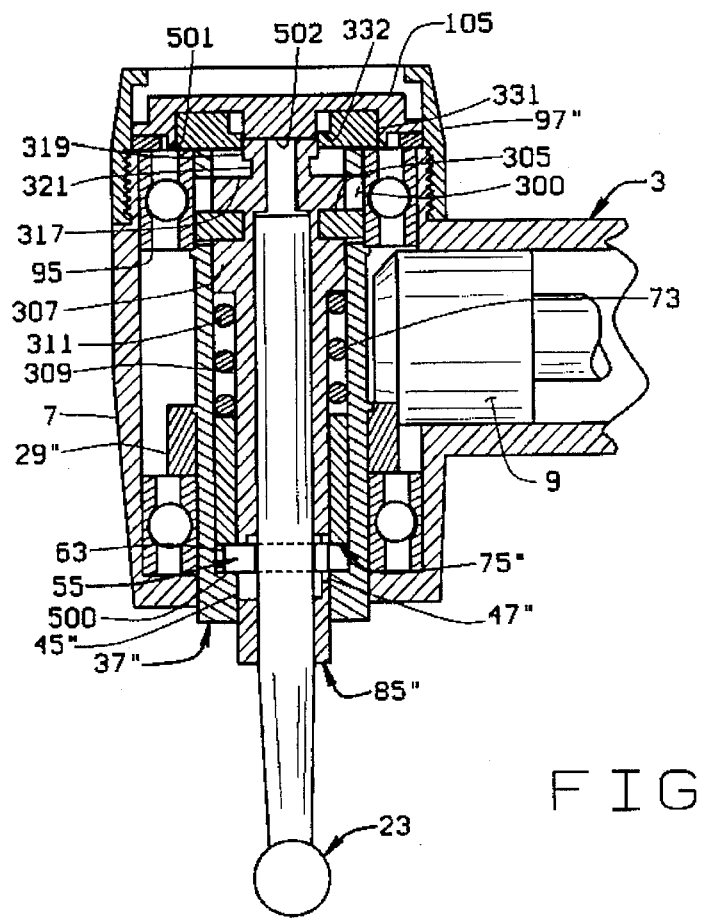
FIG. 12C
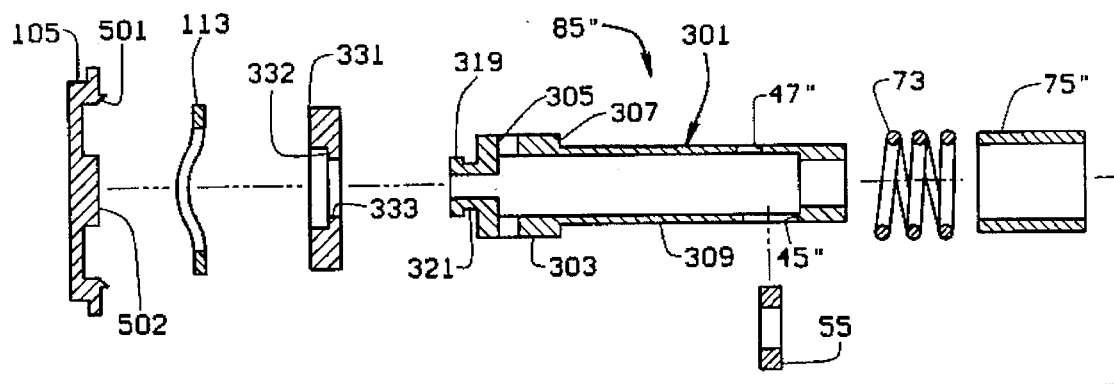
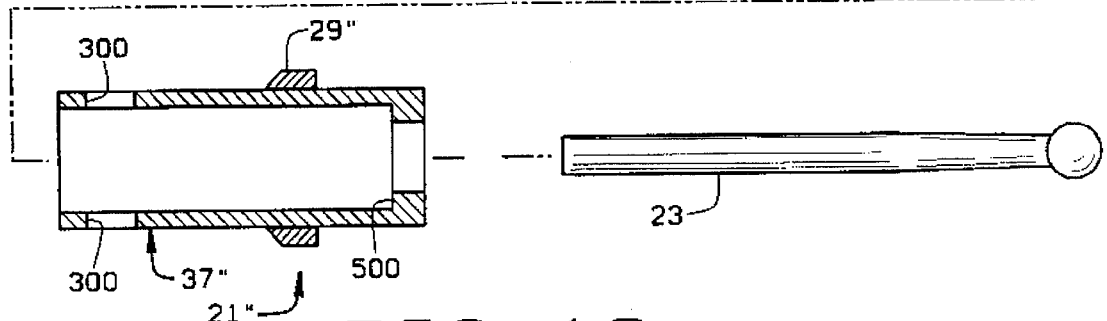
FIG. 13

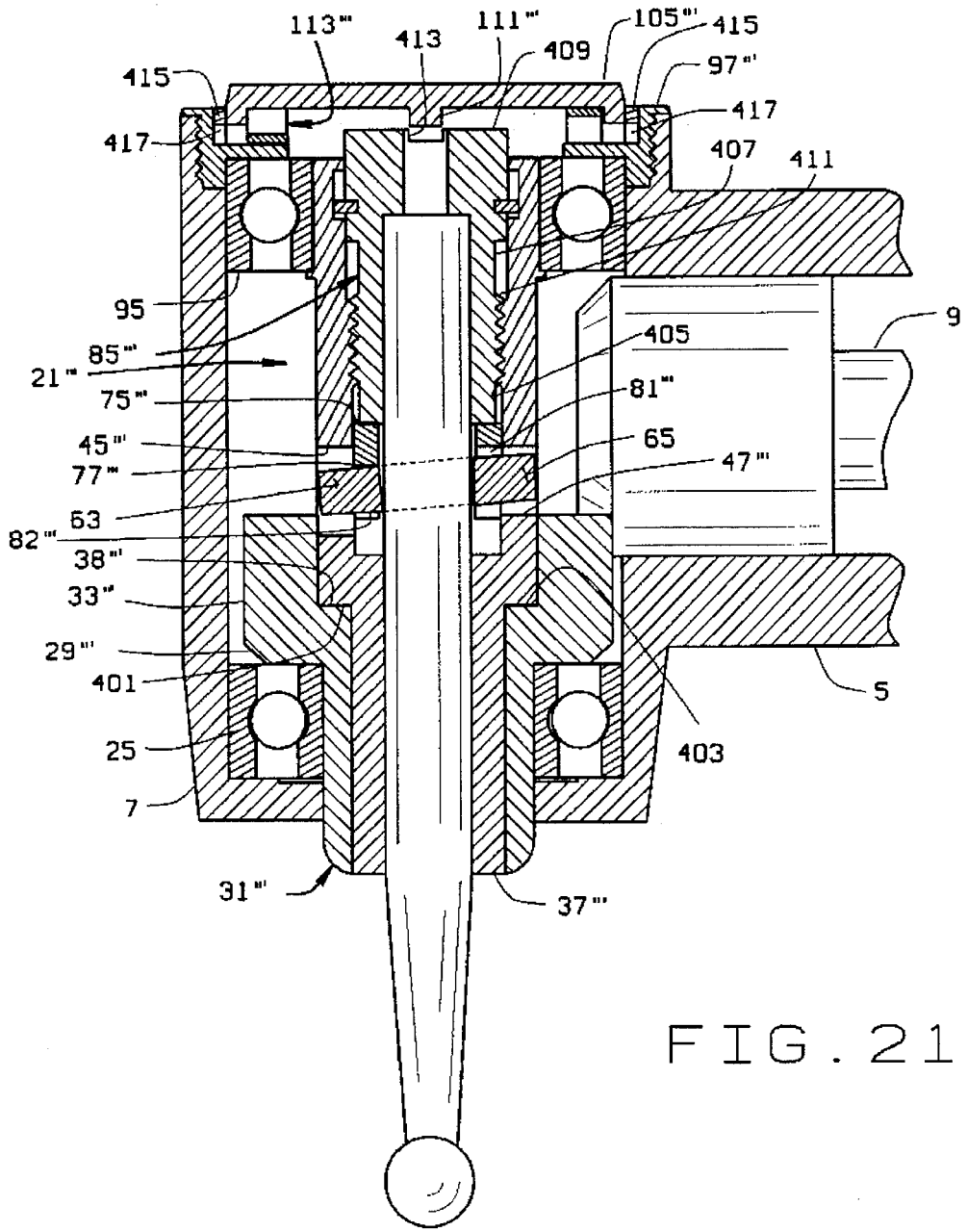
FIG.21
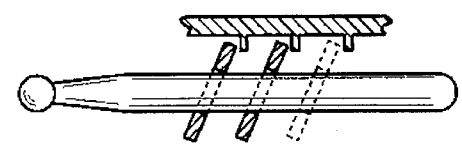
FIG.22
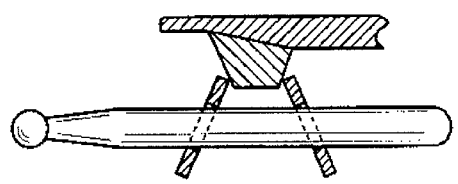
FIG.24
FIG.23
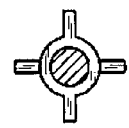
FIG.25

DENTAL TOOL CHUCK

BACKGROUND OF THE INVENTION

This invention relates to medical/dental handpieces, and in particular to a chuck for the handpiece which releasably holds and drives a cutting, polishing, or grinding tool. In its broader aspects the invention may also find application in other chucking systems which hold and rotate shafts.

Dental handpieces include both high speed turbine types (typically 200,000 to 400,000 rpm) having an air motor and gear-driven lower speed types (typically, 1,000 to 15,000 rpm) having an air motor or an electrical motor. Both have long employed collet chucks for releasably holding dental burs which cut, grind and polish teeth. Similar burs are used in surgery for performing these functions on bone. Because the shafts of dental tools are quite small and quite closely toleranced (shaft diameters between 0.0626" and 0.0630"), and because the demands of dental and surgical procedures require the utmost performance, collet chucks are high precision devices requiring a great deal of care and expense for their manufacture. The collet chucks include a tube which aligns the bur and radially movable fingers which hold the shaft of the bur both axially and rotationally. The tube, fingers, and the operating mechanism for the fingers must be formed precisely.

The chucks commonly used in dental (or surgical) handpieces generally fall into two groups: those including a positive screw thread adjustment for tightening and loosening the fingers of the chuck, and those which use a spring for tightening the chuck and some mechanism for loosening the spring. Both types of chucks have drawbacks. The threaded type requires a separate wrench which is difficult to handle, must be separately sterilized, and must be accounted for. When used with a turbine handpiece, a mechanism must be provided in the wrench or otherwise for holding the driven rotor of the turbine from rotation while turning the threaded member. The spring-biased type requires a means for opening the fingers against the spring three; a spring force great enough to hold the bur shaft reliably requires exerting a great deal of effort to open the fingers. See for example U.S. Pat. Nos. 3,637,050 to Hoffmeister, 4,874,314 to Fleer et al., 5,040,980 to Heil, and 5,090,906 to Pernot. The first two patents utilize a push button to open the chuck, and the latter two patents utilize lever arms to reduce the effort required to open the chuck. The problems with spring-biased collet chucks are described in some detail in Heil, U.S. Pat. No. 5,040,980. As further described in that patent, the force required to pull the bur shaft from the chuck when the bur is not turning is not necessarily a good predictor of how well the chuck will hold in actual use of the bur on tooth or bone. The problems are further compounded when the bur is used on disparate materials such as amalgam or the thin metal shell making up dental crowns, which can grab the bur.

Alternatives to the collet chuck have been proposed for dental angles. Examples are the expansible polyethylene sleeve shown in U.S. Pat. No. 3,324,553 to Borden, and the coil spring shown in U.S. Pat. No. 4,021,918 to Bailey. None of the alternatives, however, has provided the required precision and resistance to slippage and pull-out.

SUMMARY OF THE INVENTION

One object of the present invention is to provide a simple, effective chuck for releasably holding a dental tool in a handpiece.

Another object is to provide such a chuck which is easy to operate.

Another object is to provide such a chuck which will substantially prevent rotational and axial slippage of the tool in the chuck.

Another object is to provide such a chuck which is easy to construct and economical to produce.

Other objects will become apparent to those skilled in the art in light of the following disclosure and accompanying drawings.

In accordance with one aspect of the invention, generally stated, a chuck is provided for a dental handpiece to releasably secure a dental tool in the dental handpiece. The chuck includes a hollow bur tube which receives the dental tool. The bur tube is rotatably fixed to a driven member and has first and second aligned radial openings formed in a wall of the bur tube. The second opening is larger than the first. A tilt plate is received in the bur tube. The tilt plate has a tilt plate body, a first finger received in the first radial opening and a second finger extending through the second radial opening. A tool opening, through which the tool extends, extends generally axially through the tilt plate body. The tool opening is defined by a surface having at least one edge. The tilt plate is moveable between a first, unlocked, position in which the edge is spaced slightly from the dental tool so that the tool may be freely moved axially relative to the tilt plate, and a second, locked, position in which the edge contacts the tool to prevent axial and rotational movement of the tool relative to the tilt plate.

Preferably, a generally cylindrical tilt plate pusher is received about the bur tube. The tilt plate pusher is in operative contact with the tilt plate and is movable axially relative to the bur tube to move the tilt plate between its locked and unlocked positions. In some embodiments, a spring biases the tilt plate to its locked position, and a push button is provided which is used to operate the tilt plate pusher to move the tilt plate to its unlocked position. In another embodiment, a screw thread mechanism locks the tilt plate.

Preferably, the dental handpiece has an arm housing a drive and a head housing a driven member (generally either a gear or a turbine) in operative contact with the drive. The chuck is rotatably received in the dental tool head to be operatively connected to the driven member to be rotated by the driven member. The chuck may also be utilized in other portions of a gear-driven handpiece.

In one embodiment, the driven member has a hollow head. The bur tube is fixed to the driven member so that the driven member head and the bur tube define an annular channel. The bur tube radial openings may be positioned above the driven member or in the channel. In the former case, a spring is received in the channel, beneath the tilt plate, to operatively engage the tilt plate second finger to bias the tilt plate to its locked position. In the latter case, the tilt plate finger extends into the channel and, the tilt plate and bur tube define a second channel. In this case, the spring is located above the second finger to bias the tilt plate to its locked position. In either case, a spring spacer is preferably positioned between the spring and the tilt plate second finger. The spacer may have a slot formed therein which is aligned with the first bur tube radial opening so that the spacer does not contact said tilt plate first finger.

In a third embodiment, the tilt plate pusher is received within the bur tube.

In another embodiment, the bur tube and tilt plate pusher have engaging threads. Thus, when the tilt plate pusher is rotated in a first direction, the tilt plate pusher moves toward the tilt plate to move the tilt plate to its locked position and hold the tilt plate there. When it is rotated in the opposite direction, the tilt plate pusher is moved away from the tilt plate and the tilt plate falls to its unlocked position. The tilt plate pusher includes a top having a groove formed therein. The push button is rotatable and includes a rib which engages the tilt plate pusher groove when the push button is pushed downwardly. The push button is spring biased to be out of engagement with the tilt plate pusher. This embodiment has the benefit that it positively retains the tilt plate in its locked position.

It has been found that the chuck of the present invention provides a surprisingly firm grip on the shaft of a dental tool under operating conditions, while being easier to operate than conventional collet chucks, and that it provides the accurate and secure alignment of the bur required for dental and medical operations on calciferous structures such as tooth and bone, and for dental laboratory work.

BRIEF DESCRIPTION OF THE DRAWINGS

FIG. 2 is an exploded view of the attachment;

FIGS. 3–5 are front, side, and back elevational views of a bur tube of the attachment;

FIG. 6 is a top plan view of the bur tube;

FIGS. 12A–C are cross-sectional views of the third embodiment of the chuck, demonstrating operation of the chuck;

FIG. 13 is an exploded view of the chuck assembly of the third embodiment;

FIG. 21 is an enlarged cross-sectional view of the attachment with a fourth embodiment of the chuck:

FIGS. 22–25 are schematic drawings showing the use of two or more tilt plates in the chuck;

DESCRIPTION OF THE PREFERRED EMBODIMENT

Figure 1:
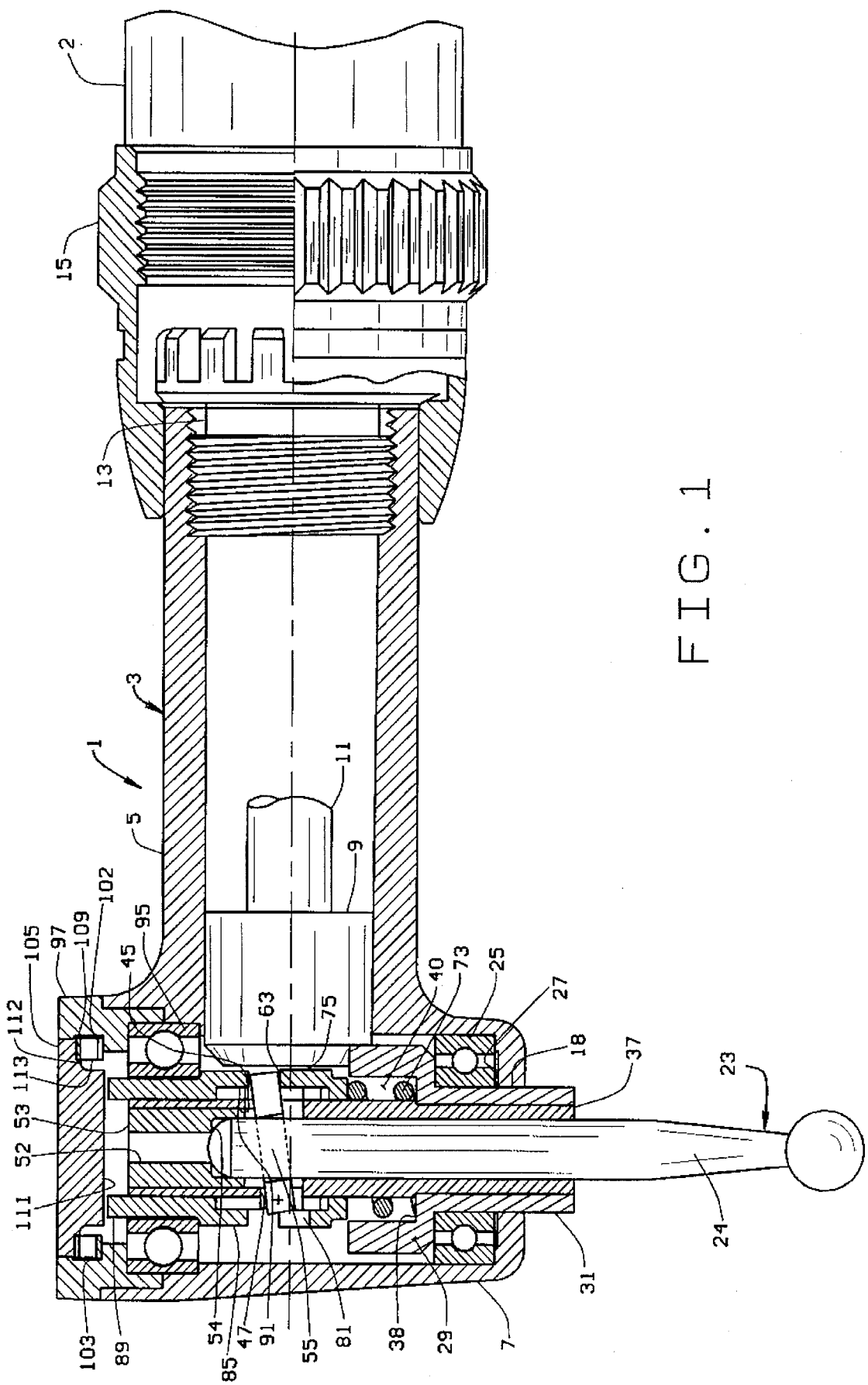
FIG. 1 is a cross-sectional view of a dental handpiece angle attachment with one illustrative embodiment of a chuck of the present invention.

A dental handpiece head assembly 1 of the present invention is shown in FIGS. 1 and 2. Assembly 1 is shown to be a dental angle and includes a one piece body 3 having a sleeve 5 and a head 7. Sleeve 5 is hollow and receives a face gear 9 which, in operation, is operatively connected to a drive system by its shaft 11. A spline knee 13 and adjusting nut 15 are secured to the back of the sleeve 5 to secure the assembly to a dental handpiece 2. Although the invention is shown incorporated into a dental angle, it will be appreciated by those skilled in the art that it could be used with other dental instruments which rotatably receive a dental tool.

Head 7 is hollow and has upper and lower openings 16 and 18, respectively. Head 7 holds a chuck assembly 21 which removably secures a dental tool 23 having a shaft 24, such as a bur, prophy cup, prophy angle, file, reamer, etc., in the head. Chuck assembly 21 is rotatably mounted in the head to drive the tool. Preferably, the chuck extends through two ball bearings 25 and 95. Ball bearing 25 sits on a shoulder 27 defined at the bottom of head 7 and which surrounds lower opening 18. Ball bearing 95 is positioned at the top of the head.

Chuck assembly 21 includes a driven gear 29 which is rotatably journaled in the bearing 25. Gear 29 has a hollow stem 31, which extends through bearing 25 and opening 18, and a head 33 having teeth 35 which mesh with drive gear 9. Head 33 is larger in diameter than stem 31 and extends radially outwardly of stem 31 and over ball bearing 25. Gear head 33 is hollow, having an annular wall 36 on which teeth 35 are formed and a floor 38 defined by the top surface of stem 31.

A hollow bur tube 37 is fixedly received in, and extends through, gear stem 31. Preferably, bur tube 37 is force fitted into stem 31 to be rotatably fixed to gear 29. Other means to rotatably fix bur tube 37 to stem 31 (such as soldering, gluing or pinning) could of course be used. Bur tube 37 removably receives tool 23. Tube 37 and gear annular wall 36 cooperate to define an annular channel 40. Bur tube 37, which is more clearly shown in FIGS. 3–6, includes a body portion 39 and a head portion 41.

A bore 42, into which tool 23 is inserted, extends through tube 37. Bore 42 has a counter-bore 42a at the top of tube 37. Body portion 39 is stepped midway up the body, as at 43, to define a shoulder 44 which sits on gear head floor 38. An opening 45 is formed in bur tube body 39 slightly below head 41. As shown, opening 45 is generally rectangular. A second, smaller, generally circular opening 47 is formed in body 39 spaced from opening 45. Opening 45, as best seen in FIG. 3, has a height greater than the height of opening 47. Counter-bore 42a extends downwardly to a point slightly below the bottom of openings 45 and 47. Head portion 41 is larger in diameter than body portion 39 and includes a pair of oppositely disposed axially extending grooves 51. Preferably, grooves 51 have a depth so that their floors are coplanar in flush with the outer wall of body 39.

A hollow plug 53 is received in bur tube bore 42a in the bur tube head 41. Plug 53 extends from the top of the bur tube to approximately the top of the bur tube opening 45. Plug 53 has a bore 52 which is counter-bored to form a shoulder 54 (FIG. 1), forming a stop which prevents tool 23 from being pushed too far into tube 37. The diameter of the counter-bore is substantially the same as the diameter of tube bore 42, both of which have a diameter slightly larger than the shaft of the dental tool to concentrically hold the dental tool in chuck 21.

Although plug 53 is preferably formed separately from bur tube 37, the plug and bur tube can be formed as a single piece. In this case, the bur tube bore 42 would be counter bored in head 41 to define shoulder 54.

A tilt plate 55 (shown more clearly in FIGS. 17 and 18) is received in bur tube 37 generally transverse to the axis of tube 37. Tilt plate 55 includes a generally annular body 57 which is sized to pass through bur tube opening 45 and be received within bore 42a. Body 57 is slightly larger in diameter than tube bore 42, thus counter-bore 42a defines a pocket in the tube which receives the tilt plate body 57. The tilt plate body 57 has an inner wall 59 defining a hole 61 through which tool 23 is slidably journaled. A first finger 63 extends radially from body 57 and protrudes through bur tube opening 45. A second smaller finger 65 extends radially from body 57 into bur tube opening 47. Due to the size differences in bur tube openings 45 and 47, finger 65 defines a pivot point for plate 55 about which tilt plate 55 can pivot vertically.

Figure 10:
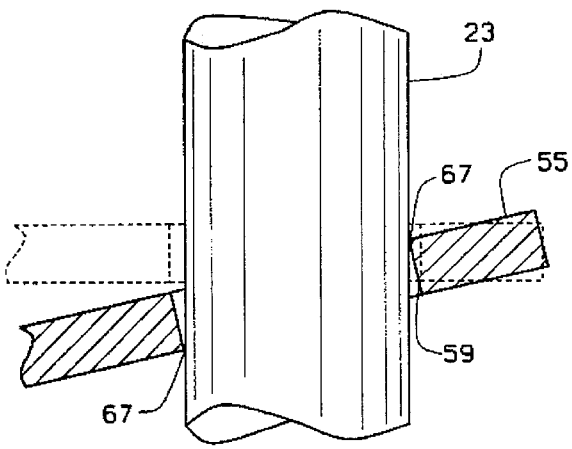
FIG. 10 is an enlarged, exaggerated schematic drawing showing the engagement of a tilt plate with a tool to hold the tool in the attachment.

As seen in FIG. 10, the tilt plate is movable between two positions. In one position, tilt plate inner wall 59 is angled with respect to the axis of tool 23 so that the edges 67 of the tilt plate wall 59 contact tool 23. This contact, as will be explained below, is strengthened or enforced so that the tool 23 is frictionally held in chuck 21 to be rotatably driven as the chuck is turned by the drive mechanism. The tilt plate's grip of the dental tool is sufficiently strong so that the tool will not move rotationally or axially relative to the tilt plate while the tool is in use. In the second position (shown in phantom) the tilt plate wall 59 is parallel to or coaxial about the tool 23 so as to be spaced therefrom. In this position, the tool can be moved relative to the tilt plate 55 so that a tool can be inserted or removed from the chuck assembly 21. Although the tilt plate wall is shown to be parallel to tool shaft 24 in the unlocked position, all that is necessary is that the edges be spaced from shaft 24 a distance sufficient to allow the tool to be moved axially.

Tilt plate wall 59 is preferably formed so that it is perpendicular to the top and bottom surfaces of the tilt plate 55. Thus, the tilt plate is in its locking position when it is tilted relative to the tool. It is in its unlocked position when plate 55 is generally perpendicular to the tool, as shown in FIG. 10. The tilt plate could alternatively be formed so that the wall 59 is not perpendicular to the tilt plate's top and bottom surfaces. In this case, the tilt plate would be in its locked position when generally perpendicular to the tool, and in its unlocked position when tilted relative to the tool. The tilt plate wall could also be formed so that the tilt plate is tilted relative to the dental tool in both its locked and unlocked positions. This difference between the preferred tilt plate and the two latter tilt plates is the angle formed by the tilt plate wall 59 and the plane of the tilt plate.

Alternatively, the tilt plate can be moved between two positions, both of which are slanted relative to the dental tool shaft. However, the edges 59 of opening 61 would be formed in the tilt plate so that they are coaxial about the dental tool in the unlocked position, and contact the dental tool when the tilt plate is pivoted to its locked position.

Figure 17:
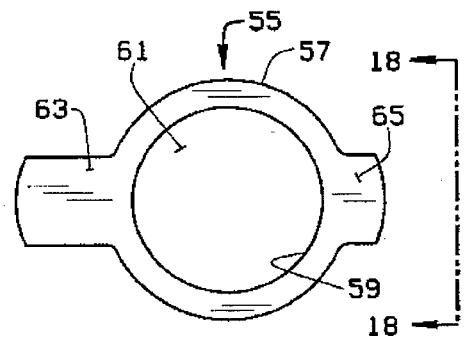
FIGS. 17–18 are top plan and side elevational views of a tilt plate used with the chuck.
Figure 18:
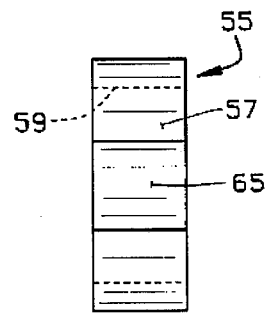
Figure 19:
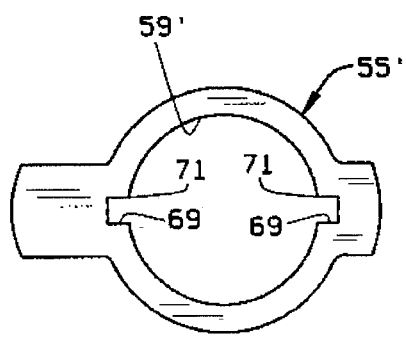
FIGS. 19–20 are top plan views showing alternate designs for the tilt plate.
Figure 20:
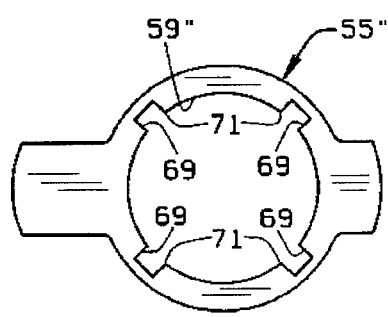

The tilt plate wall 59 of FIGS. 17 and 18 contacts the tool at only one point along each edge. It is this point of contact with the tool which "grabs" the tool to hold the tool in the tube 37. FIGS. 19 and 20 show alternate tilt plates 55' and 55". These tilt plates are substantially identical to tilt plate 55. However, their walls 59' and 59" are provided with cutouts 69. These cutouts have corners 71 which define added edges which can grab the tool to better hold the tool in the bur tube 37. As shown, tilt plate 55' has two cutouts and tilt plate 55" has four cutouts. Fewer or more cutouts could be provided and the cutouts could be differently shaped. For example, they could be shaped as triangles.

Tilt plate 55 is normally urged to its locking position by a spring 73 positioned below the tilt plate. Spring 73 is received in channel 40 and has one end seated on the floor 38 of gear head 33 and the other end in operative contact with finger 63 of the tilt plate. The spring thus urges the tilt plate finger upwardly, tilting the plate relative to the tool, biasing the tilt plate to its locked position.

Figure 8:
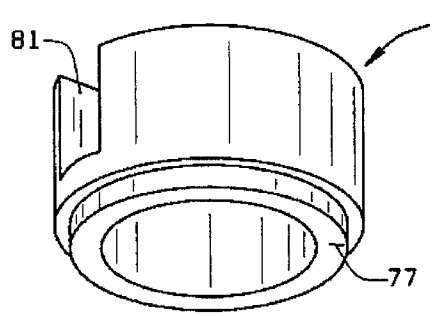
FIGS. 8 and 9 are perspective and side elevational views of a spring spacer of the attachment.
Figure 9:
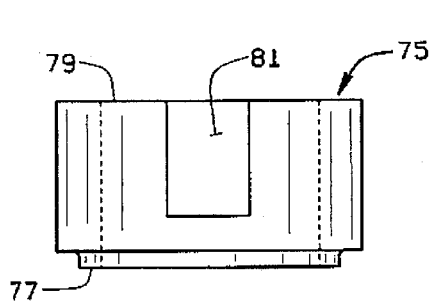

A spacer 75 (FIGS. 8–9), which is slidably journaled about bur tube 37, is positioned between spring 73 and tilt plate finger 63. Spacer 75 has a lower surface 77 against which spring 73 bears and an upper surface 79 which is in contact with the tilt plate finger 63. A slit 81 extends downwardly from spacer top surface 79, and is positioned so that it will be aligned with tilt plate finger 65. Slit 81 has a width slightly larger than finger 65 and is provided so that the spacer will not contact finger 65. This ensures that the spacer will not bear against finger 65 if it protrudes from bur tube opening 47 so that finger 65 can act as a pivot point for the tilt plate.

Figure 7:
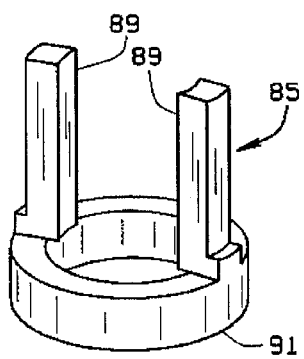
FIG. 7 is a perspective view of a tilt plate pusher of the attachment.

A tilt plate pusher 85 (shown more clearly in FIG. 7) is journaled about bur tube 37 above tilt plate finger 63. Pusher 85 has a generally cylindrical body 87 and a pair of upwardly extending arms 89. Arms 89 are slidably received in bur tube head grooves 51 to rotationally fix pusher 85 with respect to tube 37. The body 87 of pusher 85 has width approximately equal to the distance between the top of opening 45 and the bottom of bur tube head 41. The body has a lower surface 91 which, when the pusher is urged downwardly, contacts the tilt plate finger 63 to move the tilt plate from its locked (tilted) position to its unlocked (horizontal) position.

Ball bearing 95 is press fit about the top of tube 37 and is covered in the top of head 7 by a cap 97. Cap 97 has an annular wall 99 which surrounds bearing 95. Wall 99 is externally threaded so that the cap can be screwed into an internally threaded counter-bore 101 of head 7. The cap is preferably threaded into head 7 until shoulder 99a contacts the upper surface 102a of head 7. Cap 97 has a radially inwardly extending surface 103 which is adjacent the top of bearing 95. A push button 105 is received in cap 97 for axial movement. Push button 105 has a downwardly extending outer wall 109 and a pedestal 111 centrally located with respect to the wall 109. Pedestal 111 and wall 109 define a channel or shoulder 112 in which a wave spring 113 is received.. Spring 113 extends between cap surface 103 and the top of the push button channel 112 to normally bias the push button upwardly.

The push button pedestal 111 and the tilt plate pusher arms 89 are sized so that when the push button is pressed, pedestal 111 will be urged downwardly to contact arms 89 of tilt plate pusher 85. The distance of travel of the button is sufficient to urge pusher 85 downwardly a distance far enough to move tilt plate 55 from its locked to its unlocked position. When the push button 105 is released, spring 113 urges push button 105 upwardly and spring 73 urges tilt plate 55 to its locked position.

The force of the spring 73 is sufficiently strong to prevent the tool from being pulled from the bur tube and to prevent undue radial slippage of the tool within the tube while the handpiece is being operated. Chuck retention was tested in a ten minute cutting test. When the handpiece was operated at 8,000 rpm, there was virtually no axial slippage of the dental tool and no rotational slippage. When it was operated at 50,000 rpm, there was virtually no axial slippage and only slight rotational slippage. As can be appreciated, the force with which the tilt plate grabs the tool substantially prevents axial and rotational slippage of the tool at operational speeds. Further, because only light pressure is needed to depress the push button, the chuck is easily operated.

Figure 11:
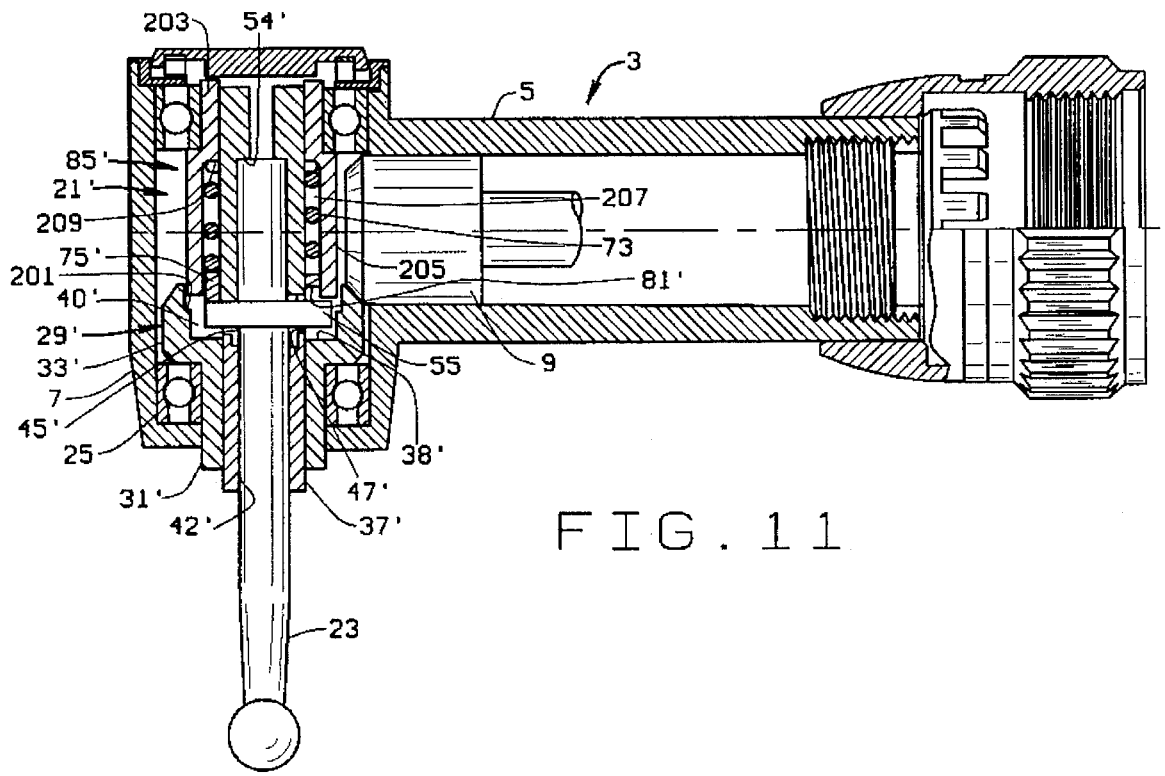
FIG. 11 is a cross-sectional view of a handpiece with a second embodiment of the chuck.

A second embodiment 21' of the chuck assembly is shown in FIG. 11. As in FIG. 1, the angle head 7 is hollow and rotatably receives a driven gear 29' which meshes with drive gear 9. Gear 29' has a hollow stem 31' which is press fitted in ball bearing 25 and a hollow head 33'. As with gear 29, head 33' has a diameter greater than stem 31' and defines a channel 40' having a floor 38'. The wall of gear head 33' is stepped to define a shoulder 201 above floor 38'. The shoulder 201 separates the inside of the hollow gear into an upper section and a lower section. The upper section has a wider diameter than the lower section to accommodate the spacer 75'

A bur tube 37' is received in gear stem 31' and extends upwardly through the head 7. Bur tube 37' has a bore 42' and a shoulder 54' formed near the top of the tube 37' to prevent the tool 23 from extending through the tube. A first opening 45' and a second smaller opening 47' are formed in tube 37' to receive tilt plate 55 in the same manner the tilt plate is received in bur tube 37, however, the openings 45' and 47' are positioned to be in the channel 40' defined by gear head 33' and bur tube 37', so that the arm 63 of tilt plate 55 extends into the channel 40'.

The tilt plate pusher 85' is journaled about bur tube 37' to slide axially with respect to tube 37'. The tilt plate pusher 85' includes an upper portion 203 which has an inner wall adjacent the bur tube 37' and a lower portion 205 which has an inner wall spaced from bur tube 37' to define a channel 207. The tilt plate pusher forms a shoulder 209 where the upper and lower portions join.

Spring 73 is received in channel 207 to extend between the tilt plate 55 and the shoulder 209 of tilt plate pusher 85'. A spring spacer 75' is inserted between the spring and the tilt plate. Spacer 75' is substantially identical to spacer 75, and includes a slot 81' so that spacer 75 will not positively contact tilt plate arm 65.

The operation of chuck 21' is similar to that of chuck 21. Chuck 21' differs from chuck 21 in that spring 73 is positioned above the tilt plate, rather than below the tilt plate. The spring 73 thus urges the tilt plate downwardly to bias the tilt plate to its normally locked position. Further, the tilt plate 55 of chuck 21' is reversed relative to tilt plate 55 of chuck 21. Arm 63 of tilt plate 55 extends through smaller bur tube opening 47' rather than 45' and short arm 65 extends through the larger bur tube opening 45'. Thus, tilt plate pusher 85' contacts the long arm 63 of the tilt plate 55 and arm 63 acts as the pivot point, rather than arm 65.

A third embodiment of the chuck is shown in FIGS. 12A–16. The angle 3 receives a chuck 21" in its head 7 which operates similarly to chucks 21 and 21' to releasably secure tool 23 therein. Chuck 21" includes a bur tube 37" press fit in ball bearings 25 and 95 to be rotatable in head 7. Bur tube 37" has openings 300 formed near the top of the tube. Preferably there are two such openings spaced 180° apart. Driven gear 29" is fixed about the bur tube 37" to mesh with drive gear 9 to rotate the chuck 21" and the tool 23. Tube 37" has an internal shoulder 500 formed at the bottom thereof.

A tilt plate pusher 85" is received within bur tube 37". It includes a head 303 having an outer diameter slightly smaller than the inner diameter of bur tube 37" so that it may slide within the bur tube and a tube 301. A hole 305 is formed in head 303 near the top thereof. As seen in FIG. 13, the hole 305 is about half the size of, and axially aligned with, the openings 300 of bur tube 37". Drive pins 306 are passed through openings 300 and 305 to rotationally fix tilt plate pusher 85" to bur tube 37". Bur tube openings 300 are axially elongate, and provide a vertical path of travel for pins 306, so that tilt plate pusher 85" may move vertically relative to tube 37" to move tilt plate 55 between its locked and unlocked positions. The outer diameter of tube 301 is stepped as at 307 to form a lower body section 309. Body section 309, with bur tube 37", defines an annular channel 311 below step 307. A pair of holes 45" and 47" are formed near the bottom of tube 301 to receive the tilt plate 55. A flange 319 is spaced above head 303 to define a groove 321 with the top 317 of tilt plat pusher head 303. Flange 319 has an outer diameter smaller than the outer diameter of bur tube 37".

Spring 73 and a spring spacer 75" are received about tilt plate pusher 85" in channel 311. Tilt plate 55 is inserted through tube openings 45" and 47" so that the spring and spring spacer are positioned above tilt plate 55 between the tilt plate and shoulder 307 of tube 85".

An offset retaining ring 331 is received in groove 321 of tilt plate pusher 85" and extends over ball bearing 95. Retaining ring 331 has an annular shoulder 332 defining an opening 333 which is partially received in groove 321. The diameter of opening 333 is slightly larger than the outer diameter of flange 319 so that the flange may slide through opening 333 when the flange is aligned with opening 333. Push button 105 is then inserted in head cap 97" above tilt plate pusher 85" so that it may push the assembly downwardly when depressed. A button spring washer 113 is received between bearing 95 and the push button 105 to urge the button normally upwardly.

Figure 12A:
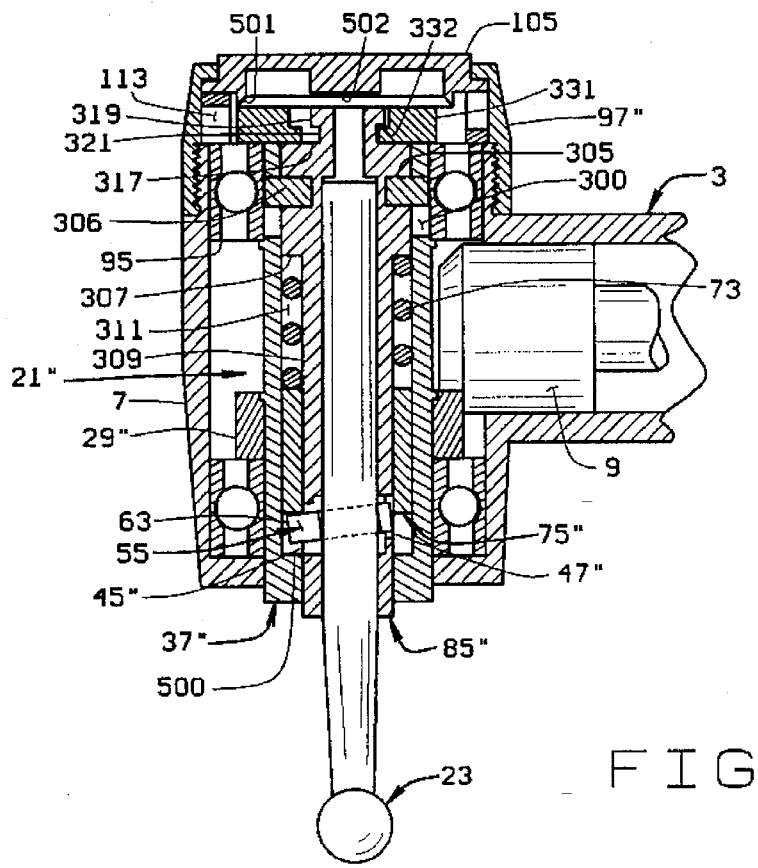
Figure 12B:
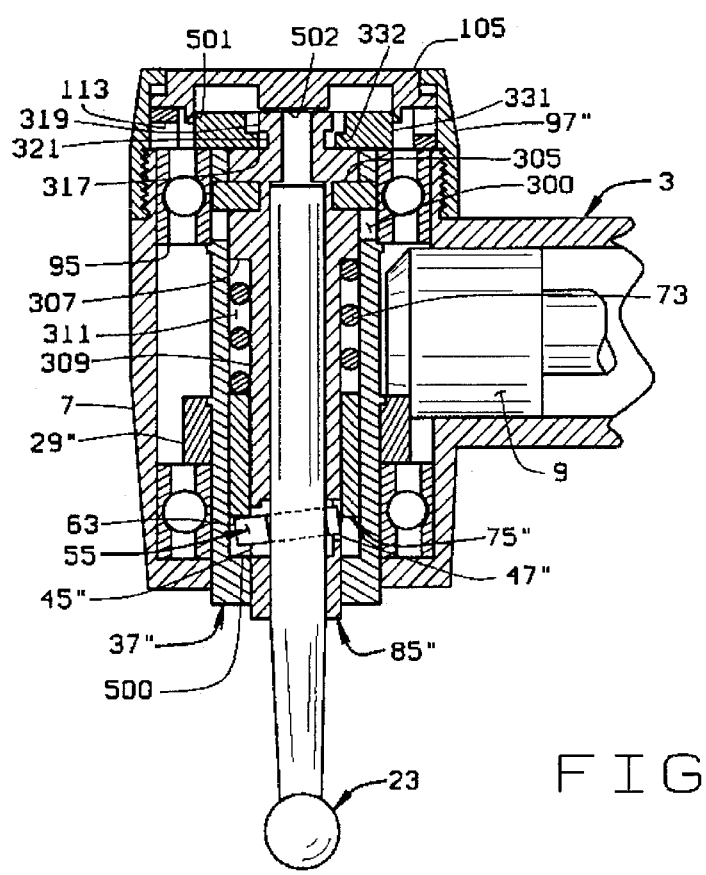
Figure 14:
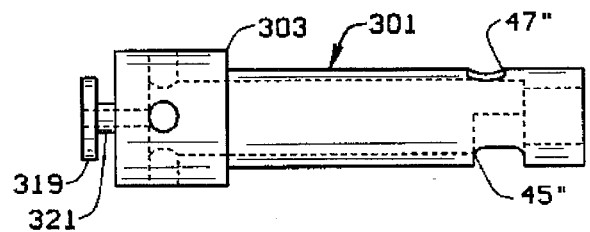
FIGS. 14 and 15 are side and front elevational views of a tilt plate pusher used with the third embodiment.
Figure 15:
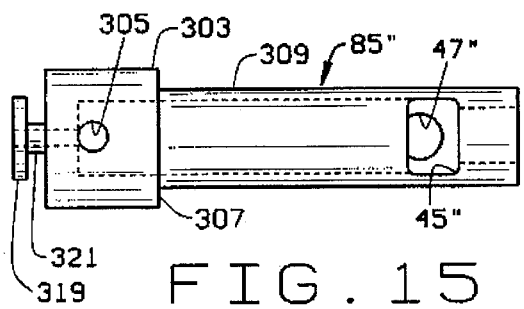
Figure 16:
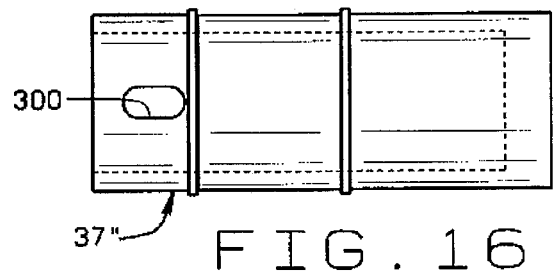
FIG. 16 is a side elevational view of an outer stationary bur tube of the third embodiment.

The operation of chuck 21" is shown in FIGS. 12A"C. When the handpiece is in use, retaining ring 331 is spun radially outwardly, causing retaining ring shoulder 332 to slide into tilt plate pusher groove 321 to hold the tilt plate pusher vertically in bur tube 37". When the operator presses down on push button 105 to release the dental tool, beveled edges 501 of the push button contact the upper edges of ring 331, to center the ring 331 and ring opening 333 with respect to the tilt plate pusher flange 319, as shown in FIG. 12B. As can be seen, the shoulder 332 and groove 321 are sized so that the shoulder 332 will not be within the groove when the retaining ring is centered. As the push button is further depressed, the push bottom pedestal 502 contacts the tilt plate pusher 85", and the tilt plate pusher is urged downwardly to urge tilt plate 55 downwardly until tilt plate arm 63 contacts bur tube shoulder 500. The tilt plate will then pivot about its arm 65 from its locked., to its unlocked, position, as shown in FIG. 12C.

A fourth embodiment 21''' of the chuck assembly is shown in FIG. 21. As before, chuck 21''' is press fit in lower and upper ball bearings 25 and 95 so that it may rotate within head 7 to rotate a tool. The chuck 21''' includes a driven gear 29''' which is substantially identical to gear 29'. However, it includes a shoulder 401 formed about halfway along its stem 31'''.

A bur tube 37''' is press fit in gear stem 31''', Bur tube 37''' is similar to bur tube 37', however, it includes a shoulder 403 which seats on gear stem shoulder 401 and internal threads 405 formed above gear 29'''. Bur tube 37''' has openings 45''' and 47''' to receive tilt plate 55 transversely in the bur tube.

A spacer 75''' is journaled internally of bur tube 37''' above tilt plate 55. Spacer 75''' has a lower surface 77''' which is in operative contact with tilt plate finger 63. A slot 81''' is provided in the wall of the spacer so that the spacer will not contact tilt plate finger 65. This allows the finger 65 to act as a pivot point for the tilt plate without interference from the spacer. A second slot 82''' is provided in spacer 75''' opposite of slot 81'''.

A tilt plate pusher 85''' is received within bur tube 37''' above spacer 75'''. Pusher 85''' is formed as a tube having a cylindrical wall 407 and a top 409. Wall 407 has external threads 411 which mesh with threads 405 of bur tube 37'''. By rotating pusher 85''' in one direction (for example counter clockwise), pusher 85''' bears down on spacer 75''', causing tilt plate 55 to tilt to its locked position, shown in FIG. 21. Because spacer 75''' is separate from pusher 85''', rotation of pusher 85''' will not cause spacer 75''' to rotate. Thus, the slot 81''' of spacer 75''' will stay in alignment with the tilt plate finger 65. If desired, spacer 75''' could be rotationally fixed to bur tube 37''', using a pin received in an elongate channel, for example, to ensure that the slot 81''' remains in alignment with the finger 65. By rotating pusher 85''' in the opposite direction (clockwise), the pusher is brought off the spacer, and the tilt plate is allowed to fall to its horizontal, unlocked position. Although not used, a spring could be provided beneath the tilt plate to bias the tilt plate to its unlocked position when the pusher 85''' is rotated to unlock the tilt plate. Unlike the chucks 21, 21', and 21", pusher 85''' places the chuck in its locked position and positively retains the tilt plate in the locked position. That is, chuck 21''' does not rely on spring forces, as do chucks 21, 21', and 21", to maintain the tilt plate in its locked position. Thus, a greater force can be exerted by the tilt plate on the tool, creating a tighter "grip" by the tilt plate of the tool.

A push button 105''' is used by the operator to rotate the pusher 85'''. Push button 105'''0 is rotatably received in a cap 97''' which closes head 7. Push button 105''' has a rib 111''' which is received in a groove 413 formed in the top 409 of pusher 85'''. Push button 105''' is biased upwardly by a wave spring 113''' which biases push button 105''' upwardly so that rib 111''' is normally out of groove 413. Thus, by pressing down on push button 105''', rib 111''' can be engaged into groove 413, and then push button 105''' is rotated to rotate the pusher 85'''. The sides of the push button 105''' could be knurled to facilitate turning of the push button, or a portion of the button 105''' could be formed as a bail to be pivoted up and used as a handle in turning the button 105'''.

Alternatively, chuck 21''' can be operated using the handpiece motor. The operator can press down on the push button to hold the tilt plate pusher against rotation, by aligning the push button rib with the tilt plate pusher groove. He can then operate the handpiece motor to turn the bur tube 37'''. This will cause the bur tube to rotate relative to the tilt plate pusher, and the tilt plate pusher will subsequently move vertically relative to the bur tube. Handpiece motors generally can be operated to run in clockwise and counterclockwise directions, and can thus be used to both lock and release the dental tool. When the dental tool is being locked in the handpiece, the push button will begin to rotate when the tilt plate reaches its locked position. By allowing for rotation of the push button at that point will prevent stripping of the push button rib and the tilt plate pusher slot, and will inform the operator that the tilt plate is in its locked position.

To prevent the push button from being rotated by the motor when the operator locks or unlocks the chuck, the push button is provided with a key 415 extending radially from the push-button vertically along its side. The key is received in a key path 417 in the cap. The interaction of the key 415 and the key path 417 will prevent the push button from rotating relative to the cap. The same goal could be achieved by using a square push button, for example. Other polygonal shaped push buttons could also be used to prevent the push button from rotating relative to the cap.

The foregoing embodiments all include a single tilt plate. The chucks could also be provided with two or more tilt plates, as shown in FIGS. 22–25. The use of two or more tilt plates increases the extent to which the tilt plates grab or bite the dental tool shaft to create a better grip on the shaft. In FIG. 22, two tilt plates are placed one on top of the other. The use of two tilt plates, as shown in FIG. 22 will not alter the operation of the chuck used. It will, however, require that the bur tube openings through which the tilt plate arms extend be enlarged to accommodate the extra thickness of two or more tilt plates.

In FIGS. 23 and 24, two spaced apart tilt plates are shown. In FIG. 23, the two tilt plates are substantially parallel and pivot in the same direction. This will require a tilt plate pusher having a side arm, as shown with inwardly directed fingers which push against the tilt plate arm when the push button is depressed to release the chuck. It will also require extra sets of bur tube openings to accommodate the spaced apart tilt plate arms.

In FIG. 24, the tilt plates pivot in opposite directions. To operate this embodiment, a spreader can be positioned between the arms that have to be spread apart to unlock the chuck. The tilt plate pusher, rather than acting directly on the tilt plates, will act on the spreader to push the spreader radially inwardly when the push button is depressed. This will cause the tilt plates to pivot to their unlocked positions. A spring can be positioned between the other arms of the tilt plates, to bias the arms apart to bias the tilt plates to a normally locked position.

In FIGS. 22–24, the tilt plates are all oriented in the same direction. That is, the tilt plate arms extend along the same vertical plane. In FIG. 25, the tilt plates are shown to be rotated with respect to each other by some degree greater than 0°. In this embodiment, the tilt plate pusher will be provided with a push arms which are spaced apart from each other to contact the arms of the respective tilt plates.

Figure 26:
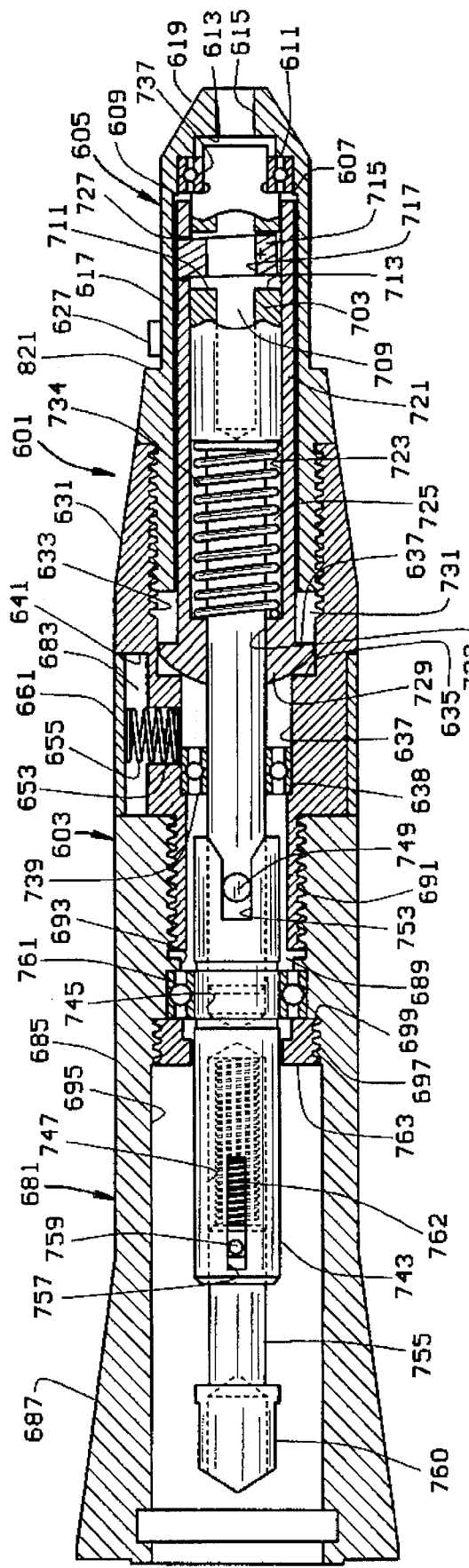
FIG. 26 is a cross-sectional view of a dental handpiece, which accepts a dental attachment, incorporating a push button release mechanism.
Figure 28:
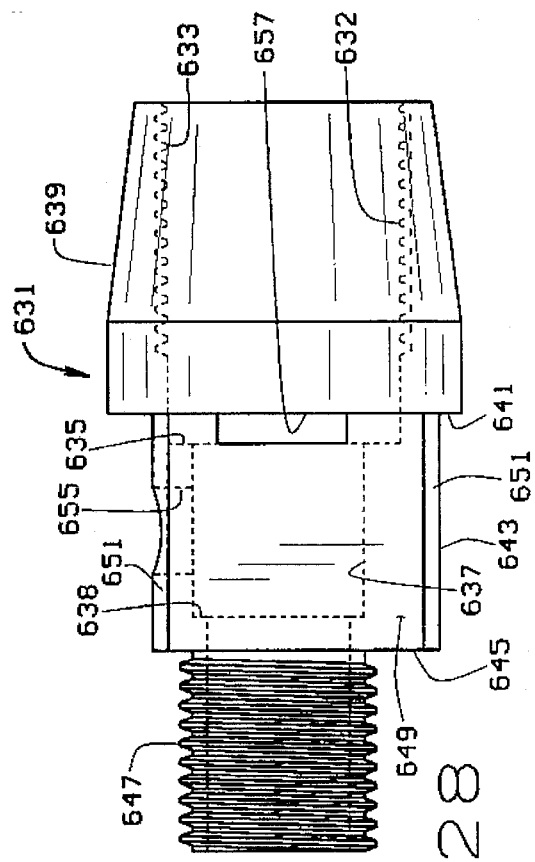
FIG. 28 is a top plan view of a center sheath of the handpiece.
Figure 27:
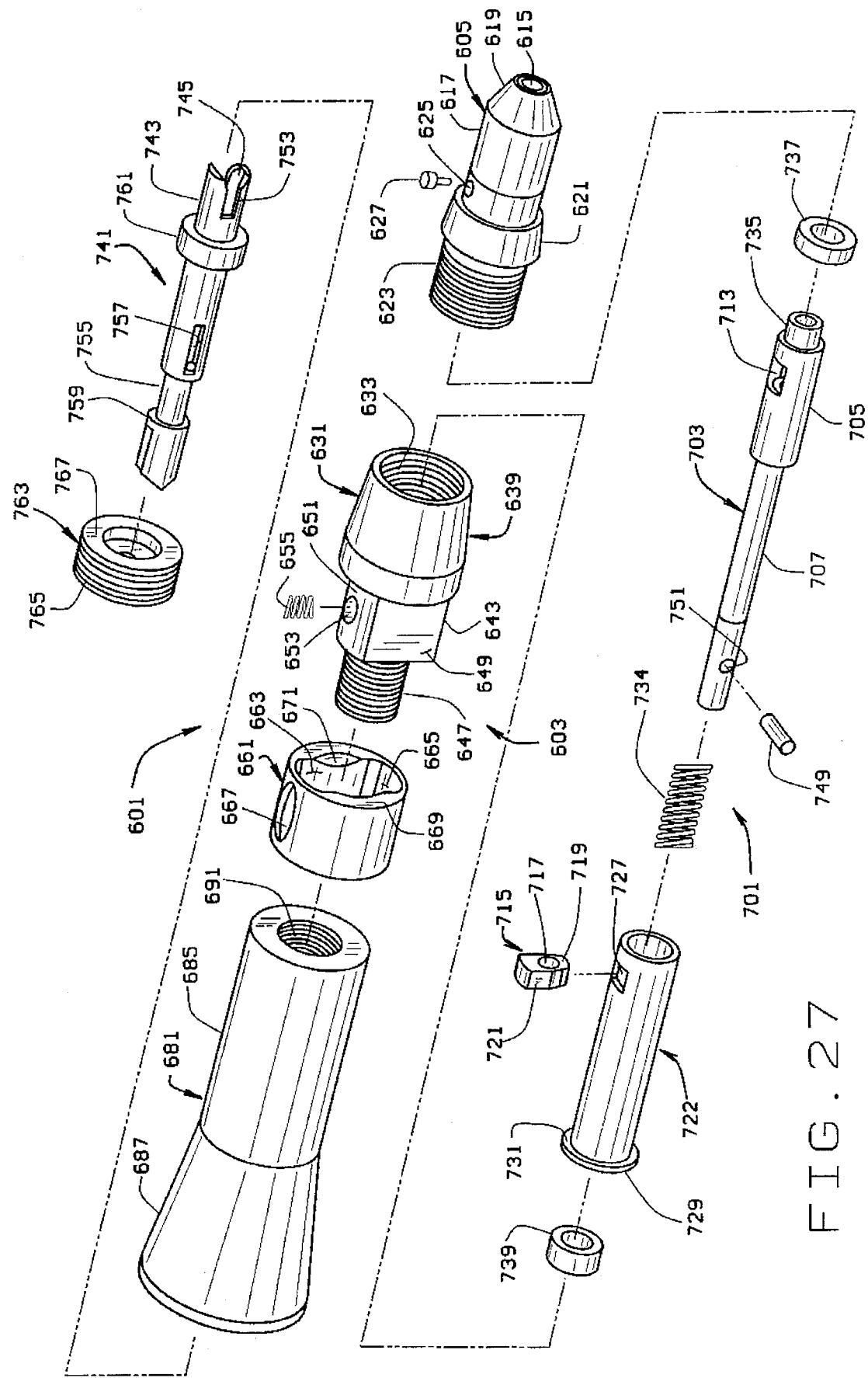
FIG. 27 is an exploded view of the handpiece of FIG. 26.

Turning to FIGS. 26–28, a dental handpiece 601 is shown which incorporates a push button chucking mechanism to quickly and easily releasably secure the shaft of a dental tool or attachment. Hand piece 601 includes a multi-part sheath 603 which defines the outer surface of the handpiece. A front sheath or head 605 has an axial bore 607 which is stepped inwardly as at 609, 611, and 613, culminating in a forward opening 615 at the front of the sheath 605 into which a shaft of a dental tool can be inserted. This shaft can be the shaft of bur, such as bur 23, shown in FIG. 1. It can also be the shaft 11 extending rearwardly from the drive gear 9 of FIG. 1. Externally, front sheath 605 defines a body 617 having a tapered front end 619. A circumferential flange 621 is formed midway along the length of sheath 605 and has a sloped outer surface. Rearwardly of flange 621, sheath 605 is externally threaded, as at 623. Forwardly of flange 621, a bore 625 is formed which receives an orientation pin 627. Pin 627 functions to prevent attachments, such as prophy angles, from rotating on the handpiece during use, as is known in the art.

A center sheath or arm 631 threadedly receives front sheath 605. Sheath 631 is hollow, defining a bore 632 having an internally threaded front portion 633 into which threaded portion 623 of sheath 605 is screwed. Sheath 631 is stepped internally, as at 635 to define a bore 637. An internal shoulder 638 is defined in bore 637, near the back thereof. Externally, the front portion 639 of center sheath 631 is sloped to form a smooth transition with the outer surface of front sheath 605. Sheath 631 is stepped at 641 to define a center section 643, and at 645 to define a back portion 647 which is externally threaded. Center portion 643 has two opposing flat sides 649 which are joined by arced surfaces 651. A blind bore 653 is formed in one of the surfaces 651 to receive a spring 655. As can be seen best in FIGS. 26 and 28, rear portion 647 is not centered with respect to center portion 643. The shoulder 645, which forms the back surface of center portion 643, has a bottom which extends farther from the center of bore 637 than does the top of the shoulder; top and bottom being made with reference to the drawings. The bore 653 is formed in the top arced surface 651. Generally rectangular openings 657 are formed at the front of center section 643 on flat surfaces 649. Preferably, openings 657 extend rearwardly from shoulder 641.

A push button 661 is slidably received about center section 643 of sheath 631. Push button 661 defines a generally hollow cylinder which has opposing flat inner surfaces 663 joined by arced surfaces 665. The length of push button surfaces 663 are larger than sheath center section surfaces 649, so that push button 661 may slide vertically relative to center section 643. Push button 661 is biased upwardly by spring 655, as shown in FIG. 26. The outer circumference of push button 661 is substantially equal to the outer circumference of center sheath forward section 639, and spring 655 operates to normally maintain push button in this position. Push button 661 has an indentation 667 formed in the top thereof, which is positioned to be above spring 655. Indentation 667 defines an indicia which informs the operator where to press the push button to operate the chuck, as will be described below.

Push button 661 has a front surface 669 having an arced or chamfered cutout 671 formed in front surface 669 at the junction between surface 669 and internal flat surfaces 663. Cutout 671 is positioned to be centered over opening 657 in sheath center section 643 when the push button is in its normal position. The surface of cutout 671 preferably defines a segment of a sphere. Preferably, there are two such cutouts 671, one for each sheath opening 657.

A rear sheath 681 is threadedly secured to the center sheath threaded portion 647 and is screwed onto the center sheath to abut center sheath shoulder 645. Rear sheath 681 has an outer diameter, at the front thereof, substantially equal to the outer diameter of the back of the center sheath's forward portion 639. The rear sheath is spaced from the center sheath forward portion, and the two pans cooperated to define an annular slot 683 in which the push button slides. Rear sheath 681 has a generally cylindrical forward portion 685 and a flared back portion 687. Sheath 681 has a forward bore 689 which is threaded, as at 691, at the front thereof. At the back of threads 691, a flange 693 extends radially inwardly, into bore 689. Rearwardly of bore 689, sheath 681 defines a larger diameter bore 695 having internal threads 697 at its front. Bore 695 ends in a forward front shoulder 699 which separates bores 689 and 695. Bore 695 is sufficiently wide so that sheath 681 may be slidably placed over a dental motor unit, to be secured thereto, as is known in the art.

Sheath 603 rotatably houses a chuck 701 which releasably receives the shaft of a dental tool or attachment. Chuck 701 includes a bur tube 703 having a head 705 and a rearwardly extending shaft 707. Head 705 is hollow, defining a bore 709 sized to receive the dental tool or attachment shaft. As in the bur tubes of FIGS. 1 and 11, bur tube head 705 has a first large opening 711 and a second smaller opening 713 which receives a tilt plate 715. Tilt plate 715 has an opening 717 through which the dental tool or attachment shaft extends. A first arm 719 of tilt plate 715 is received in larger head opening 711 and extends through smaller head opening 713. A longer arm 721 of plate 715 is received in larger head opening 711. Because the openings 711 and 713 are of different sizes, tilt plate 715 can be tilted, as will be explained below, to move between a position in which the walls, defining opening 717, are substantially coaxial about the dental tool shaft to allow the dental tool to be placed on or removed from the handpiece 601, and a second position in which the walls defining the opening 717 are oriented to engage, or bite into, the dental tool or attachment shaft, to secure the shaft in the chuck for use.

A tilt plate pusher 722 is slidably received about bur tube 703. Tilt plate pusher 722 is substantially hollow, defining a bore 723 which extends from the front of tilt plate pusher 722 to a point near the back of the tilt plate pusher. Bore 723 has a diameter slightly larger than the diameter of bur tube head 705, so that the tilt plate pusher may slide over the bur tube head. The diameter of bore 723 is, however, larger than the bur tube shaft 707, and defines an annular channel 725 with the shaft. Tilt plate pusher 722 has an opening 727 through which tilt plate arm 721 extends. At its back end, tilt plate pusher 722 has a head 729 having a substantially semi-spherical outer surface. Head 729 is larger in diameter than the outer diameter of pusher 722, and defines a shoulder or flange 731. When the handpiece 601 is assembled, flange 731 extends through openings 657 in center sheath 631, as will be described below. Tilt plate pusher head 729 has a bore 733 which is coaxial with tilt plate pusher bore 723. Bur tube shaft 707 slidably extends through head bore 733 to extend rearwardly of head 729.

A spring 734 is received in the annular channel 725 defined by the inner surface of tilt plate pusher bore 723 and bur tube shaft 707. Spring 734 is seated, on one end, against the back surface of bur tube head 705, and at another end, against a shoulder 736 at the back of bore 723. When the handpiece is assembled, spring 734 normally urges tilt plate pusher 722 rearwardly.

Bur tube 703 has a portion 735 forward of, and narrower than, bur tube head 705. To rotatably secure chuck 701 in sheath 603, a forward bearing 737 is press fit about the bur tube forward portion 735. A rear bearing 739 is press fit on bur tube shaft 707 intermediate the ends of the shaft. When the handpiece is assembled, the front bearing 737 is seating on shoulder 611 in the front sheath 605, and the rear bearing 739 is seated against the shoulder 638 in center sheath 631. As can be appreciated, the chuck 701 is sized to fit within the front and center sheaths 605 and 631.

A drive connector 741 is provided to connect the chuck 701 to the drive. Drive Connector 741 includes a tube 743 having a forwardly opening bore 745 and a rearwardly opening bore 747. Bore 745 is sized to slidably receive bur tube shaft 707. To rotatably fix bur tube 703 to connector 741, a pin 749 is passed through a hole 751 near the back of shaft 707. Tube 743 has a pair of axially extending slots 753 though which pin 749 slidably extends. Slots 753 preferably open to the front of tube 743 to facilitate connection of the drive connector 741 to bur tube shaft 707, but may be made to be closed, if desired. A connector shaft 755 is slidably received in connector rear bore 747 and extends rearwardly from the connector. Connector tube 743 has a pair of slots 757. A pin 759 extends though slots 757 and shaft 755 to rotatably fix shaft 755 to connector tube 743. Shaft 755 has a rear head 760 which is grasped by the drive, in a manner known in the art, to rotatably drive the connector, chuck, and hence the dental tool or attachment. A spring 762 is received in connector tube rear bore 747 to bias shaft 755 outwardly. As seen in FIG. 26, pin 759 slides in slot 757. Slot 757 is closed, and thus, spring 762 cannot push shaft 755 out of bore 747. Connector 741 could be made as a single piece. However, various drives may extend into the rear sheath 681 to varying depths. Thus, connector 741 is designed to have a variable length. The use of spring 762 will urge shaft 755 normally outwardly, and the drive can urge the shaft inwardly, if necessary. A third bearing 761 is press fit about tube 743 and is positioned on tube 743 so that it will slidably seat against shoulder 693 in rear sheath bore 689. A lock nut 763, having external threads is threaded onto threads 697 in rear sheath bore 695 until lock nut abuts shoulder 699. Lock nut 763 has a forward surface 767 having an annular width larger than the width of shoulder 699. Lock nut 763, thus holds bearing 761, and hence connector 741, is placed in sheath 603.

To assemble handpiece 601, front bearing 737 is press fit on bur tube front portion 735. Spring 734 is placed about bur tube shaft 707 and the tilt plate pusher 721 is place over bur tube 703. Tilt plate 715 is then passed through tilt plate pusher opening 727 and into bur tube 703, through bur tube opening 713. Bearing 739 is press fit on shaft 707 and pin 749 is pressed through bur tube shaft 707. The chuck 701, is the inserted into front sheath 605 so that front bearing 737 rests against shoulder 611. The center sheath 631 is secured to front sheath 605, so that back bearing 739 is seated against shoulder 638 to secure chuck 701 in the sheath. When the chuck is in place in the sheath, tilt plate pusher head 729 extends through center sheath openings 657. Spring 655 is inserted in center sheath bore 651, and push button 661 is slid over center sheath center portion 643. The rear sheath 681 is then secured to center sheath 631 to secure push button 661 in place.

Drive connector 741 is slidably placed in rear sheath 681 so that bearing 761 sits on flange 693. Connector 741 is then secured in sheath 681 by lock nut 763. Connector 741 may be placed in sheath 681 either before or after the rear sheath is secured to the center sheath.

To operate the chuck, the push button 661 is depressed in channel 683. When the push button is depressed, the push button chamfered edges 671 will slide against tilt plate pusher head 729 to urge the tilt plate forward. When the tilt plate is urged forward, the rear edge of tilt plate pusher opening 727 will contact tilt plate arm 721 and move the tilt plate to its first, unlocked position, to allow a dental tool or attachment to be inserted in, or removed from, bur tube 703. When the push button is released, spring 655 will urge the push button upwardly to its normal position. Because bur tube 703 is axially fixed in sheath 603, spring 734, in channel 725, will then urge tilt plate pusher rearwardly. The front edge of tilt plate pusher opening 727 will then contact tilt plate arm 721 and move the tilt plate to its tilted, locking position, to secure a dental tool or attachment shaft in the bur tube.

As can be appreciated, the preferred embodiments provide for a chuck which is easy to operate. Importantly, the head is closed, except for the bottom of the head where the tool is inserted, so that few to no contaminants can enter the head 7.

As variations within the scope of the appended claims may be apparent to those skilled in the art, the foregoing description is set forth only for illustrative purposes and is not meant to be limiting. For example, although the chuck of the present invention has been described in a gear driven system, it will be appreciated that it could be used equally well in a turbine driven system. All that need be done is to replace the driven gear with turbine blades and provide an air tube through the sleeve of the handpiece to deliver driving air to the turbine blades. Spring spacer 75 facilitates application of the spring force exerted by spring 73. The spring spacer, however, could be deleted from the chuck assembly. In the fourth embodiment, more than one rib can be provided on the under surface of the push button which will be received by an equal number of grooves formed in the tilt plate pusher. The increased number of ribs and grooves may create a better hold of the push button on the tilt plate pusher. In the handpiece of FIGS. 26–28, the chuck could be designed so that the tilt plate pusher slides inside of the bur tube, rather than outside of the bur tube as shown. The push button of the spring-loaded embodiments may equivalently be replaced by a camming lever such as the lever of the above-mentioned Heil U.S. Pat. No. 5,040,980. It will also be apparent to those skilled in the art that the chucks of the present invention could be used in conjunction with medical instruments, such as surgical drills. These examples are merely illustrative.

We claim:

1. A medical/dental device for rotatably driving a dental tool, the device including an arm and a head formed at an end of said arm; said arm delivering a drive member to said head; said head defining a chamber in communication with said arm, a driven member in said head chamber to be driven by said drive member, said head having a tool receiving end and a top end, said dental tool being removably receivable in said driven member and extending out said tool receiving end, a chuck, rotatably fixed to said driven member, which releasably holds said dental tool in said device; said chuck including:

a hollow bur tube received in said head chamber, said bur tube being operatively connected to said driven member, said bur tube being sized to slidably receive a shaft of said dental tool;

at least one tilt plate received internally of said bur tube and having an opening therein through which said dental tool extends, said opening being defined by a surface having at least one edge, said tilt plate being pivotally moveable between a first, unlocked, position in which said edge is spaced slightly from said dental tool so that said tool may be freely moved axially relative to said tilt plate, and a second, locked, position in which said edge contacts said tool to prevent movement of said tool relative to said tilt plate; and a tilt plate pusher operable to move said tilt plate between its locked and unlocked positions;

wherein at least one of said tilt plate pusher and said bur tube includes at least one radial opening therein; said tilt plate having a radially extending finger which is at least partly received in said at least one radial opening, said finger defining a pivot point about which said tilt plate axially pivots in said chuck.

2. The device of claim 1 wherein said at least one radial opening comprises a first radial opening and a second radial opening formed in a wall therein, said second opening having an effective axial length greater than said first opening; said second opening sized to allow passage of said tilt plate therethrough.

3. A medical/dental device for rotatably driving a dental tool, the device including an arm and a head formed at an end of said arm, said head defining a chamber; said arm housing a drive means and said drive means being at least partially received in said head; said head chamber being in communication with said arm, a driven means in said head chamber to be driven by said drive means, said head having a tool receiving end and a top end, said dental tool being removably receivable in said driven means and extending out said tool receiving end, a chucking device, rotatably fixed to said driven means, which releasably holds said dental tool in said medical/dental device; said chucking device including:
- a hollow bur tube received in said head, said bur tube being operatively connected to said driven means, said bur tube being sized to slidably receive a shaft of said dental tool:
- at least one tilt plate received internally of said bur tube and having an opening therein through which said dental tool extends, said opening being defined by a surface having at least one edge, said tilt plate being moveable between a first unlocked, position in which said edge is spaced slightly from said dental tool so that said tool may be freely moved axially relative to said tilt plate, and a second, locked position in which said edge contacts said tool to prevent movement of said tool relative to said tilt plate; and
- a tilt plate pusher operable to move said tilt plate between its locked and unlocked positions;
- wherein one of said tilt plate pusher and said bur tube has a first radial opening and a second radial opening formed in a wall therein, said second opening having an effective axial length greater than said first opening; said second opening sized to allow passage of said tilt plate therethrough; wherein said tilt plate has a first finger extending through said first opening and a second finger received in said second opening, said first finger defining a pivot point about which said tilt plate axially pivots in said chuck.

4. The device of claim 3 wherein said tilt plate opening surface is perpendicular to the plane of said tilt plate, wherein said tilt plate is generally perpendicular to said dental tool when said tilt plate is in said unlocked position and said tilt plate is tilted relative to said dental tool when said tilt plate is in said locked position.

5. The device of claim 3 wherein said tilt plate hole surface is diagonal relative to the plane of said tilt plate, wherein said tilt plate is generally perpendicular to said dental tool when said tilt plate is in said locked position and said tilt plate is tilted relative to said dental tool when said tilt plate is in said unlocked position.

6. The device of claim 3 wherein said tilt plate pusher comprises a tube which is received in said bur tube, said tilt plate pusher and said bur tube having engaging threads such that rotation of one of said tilt plate pusher and said bur tube relative to the other in a first direction moves said tilt plate pusher downwardly relative to said bur tube, and rotation in a second direction moves said tilt plate pusher upwardly relative to said bur tube.

7. The device of claim 6 wherein said tilt plate pusher is positioned above said tilt plate whereby rotation in said first direction urges a lower edge of said tilt plate pusher into operative contact with said second tilt plate finger to place said tilt plate in its locked position, said device further including an annular spacer journaled about said bur tube and positioned between said tilt plate pusher and said tilt plate.

8. The device of claim 7 wherein said spacer includes a slot formed in a wall thereof, said slot being aligned with said first radial opening so that said first tilt plate finger will not be contacted by said spacer.

9. The device of claim 8 including a push button which releasably operatively engages said tilt plate pusher to operate said tilt plate pusher, said push button having an outer surface, an inner surface, and at least one rib extending along said inner surface; said tilt plate pusher having a groove shaped complementary to said push button rib, said rib engaging said groove when said push button is depressed.

10. The device of claim 9 including a spring which biases said push button upwardly so that said rib is normally out of engagement with said tilt plate pusher groove.

11. The device of claim 9 wherein said push button includes a knurled outer surface to facilitate rotation of said push button, and hence rotation of said tilt plate pusher when said push button rib engages said tilt plate pusher groove.

12. The device of claim 9 including a cap received on said head and wherein said drive means is operated to rotate said tilt plate pusher relative to said bur tube when said push button rib is engaged in said tilt plate pusher groove, said push button including a finger extending from a side of said push button, said finger being received in a groove in said cap, said finger and cap cooperating to prevent rotational motion of said push button relative to said cap.

13. The device of claim 3 including a spring which biases said tilt plate to its locked position.

14. The device of claim 13 including an externally accessible push button operable to move said tilt plate pusher from a first position in which a bottom of said tilt plate pusher is spaced from said tilt plate, said tilt plate being in said locked position, to a second position in which said tilt plate pusher bottom contacts said tilt plate and moves said tilt plate from its locked position to its unlocked position.

15. The device of claim 14 wherein a spring spacer is received between said spring and said tilt plate.

16. The device of claim 15 wherein said spring spacer has a slot formed therein, said slot being aligned with said first radial opening so that said spacer does not contact said tilt plate first finger.

17. The device of claim 14 wherein said tilt plate pusher receives said bur tube; said radial openings being formed in said bur tube; said bur tube being fixed in said driven means; said driven means having a hollow head, said bur tube and said driven means head cooperating to define an annular channel.

18. The device of claim 17 wherein said spring is received in said channel below said tilt plate.

19. The device of claim 17 wherein said tilt plate is at least partially received in said annular channel; said tilt plate pusher having a portion thereof which is radially spaced from said bur tube to define a second annular channel with said bur tube, said spring being received in said second annular channel above said tilt plate.

20. The device of claim 14 wherein said tilt plate pusher and said tilt plate are received in said bur tube, said first and second radial openings being formed in said tilt plate pusher, said bur tube having a portion thereof radially spaced from said tilt plate pusher to define an annular channel with said tilt plate pusher, said spring being received in said annular channel.

21. A push button operated chuck for releasably securing a tool in a medical/dental device, said chuck being rotatably received in said device in operative contact with a drive in said device to be rotated by said drive; said chuck including:
- a hollow bur tube which receives said tool, said bur tube defining a first radial opening and a second larger radial opening in a wall thereof;
- a tilt plate received internally of said bur tube; said tilt plate having a tilt plate body, a first finger received in said first radial opening and a second finger extending through said second radial opening, and a tool opening extending generally axially through said tilt plate body; said tool extendable through said tool opening; said tool opening being defined by a surface having at least one edge; said tilt plate being pivotal between a first, unlocked, position in which said edge is spaced from said tool so that said tool may be freely moved axially relative to said tilt plate, and a second, locked, position in which said edge contacts said tool to prevent axial and rotational movement of said tool relative to said tilt plate, one of said first and second fingers of said tilt plate defining a pivot point for said tilt plate about which said tilt plate pivots; and a tilt plate pusher telescoping relative to said bur tube, said tilt plate pusher being in operative contact with said tilt plate and being movable axially relative to said bur tube to pivot said tilt plate between its locked and unlocked positions.

22. The chuck of claim 21 including a push button which operatively engages said tilt plate pusher to move said tilt plate between its locked and unlocked positions.

23. The chuck of claim 22 wherein said tilt plate pusher comprises a tube which telescopes relative to said bur tube; said tube having a top surface; said tilt plate pusher and said bur tube having engaging threads such that rotation of one of said tilt plate pusher and said bur tube relative to the other in a first direction moves said tilt plate pusher downwardly relative to said bur tube, and rotation in a second direction moves said tilt plate pusher upwardly relative to said bur tube; said tilt plate pusher being positioned above said tilt plate whereby rotation in said first direction urges a lower edge of said tilt plate pusher into operative contact with said first tilt plate finger to place said tilt plate in its locked position.

24. The chuck of claim 23 wherein said push button is rotatable, said push button having an inner surface with at least one rib thereon; said tilt plate pusher having a groove shaped complementary to said push button rib, said rib engaging said groove.

25. The chuck of claim 24 including a spring which biases said push button upwardly so that said rib is normally out of engagement with said tilt plate pusher groove, said push button rib engaging said groove only when said push button is depressed.

26. The chuck of claim 25 including an annular spacer telescoping relative to said bur tube and positioned between said tilt plate pusher and said tilt plate, said spacer including a slot formed in a wall thereof, said slot being aligned with said first bur tube radial opening so that said first tilt plate finger will not be contacted by said spacer.

27. The chuck of claim 22 wherein said bur tube is received in a driven member which is operatively connected to said drive to be rotated thereby, said driven member having a hollow head, said driven member head and said bur tube defining an annular channel, said chuck including a spring which normally biases said tilt plate to its locked position.

28. The chuck of claim 27 wherein said bur tube radial openings and said tilt plate are spaced above said driven member, said spring being received in said channel which biases said tilt plate to its locked position.

29. The chuck of claim 27 wherein said bur tube radial openings are positioned to be in said channel, said tilt plate fingers extending into said channel.

30. The chuck of claim 29 wherein said tilt plate pusher defines an upper section having an inner diameter which abuts an upper portion of said bur tube and a lower section radially spaced from said bur tube, said bur tube and said tilt plate pusher lower section defining a second channel, said spring being received in said second channel above said tilt plate.

31. The chuck of claim 30 including a spring spacer positioned between said spring and said tilt plate second finger.

32. The chuck of claim 31 wherein said spring spacer has a slot formed therein, said slot being aligned with said first radial opening so that said spacer does not contact said tilt plate first finger.

33. A method of releasably holding a shaft in a medical/dental handpiece, said handpiece including a tilt plate, a tilt plate pusher and a tube, one of said tilt plate pusher and said tube being received in the other of said tilt plate pusher and said tube, said tilt plate pusher and said tube being movable axially relative to each other, one of said tilt plate pusher and said tube defining an opening in a wall thereof, said tilt plate including at least one finger which is at least partially received in said opening, said method comprising a step of inserting the shaft into said tube in the handpiece and through an opening in the tilt plate in the handpiece, and thereafter a step of pivoting the tilt plate about a pivot point to a locked position to engage the shaft with at least one edge of a wall defining the opening in the tilt plate; the pivot point being defined by said finger.

34. The method of claim 33 wherein said tilt plate is spring biased to said locked position, said method including a step of removing said shaft by moving the tilt plate against the spring bias from said locked position.

35. The method of claim 33 wherein said tilt plate pusher and said tube are threadedly engaged; said method including rotating said tilt plate pusher relative to said tube to move said tilt plate pusher relative to said tube.

36. The method of claim 35 wherein said handpiece includes a push button, the push button including a rib and said tilt plate pusher includes a groove, said rib being received in said groove when said push button is pressed; said method including rotating said push button when said push button is depressed to rotate said tilt plate pusher relative to said tube.

37. The method of claim 33 wherein the shaft is the shaft of a bur, the step of inserting the shaft into the handpiece including inserting the shaft into a head of an angle part of the handpiece.

38. A medical/dental handpiece including at least a first part telescoped within a second part, said handpiece comprising a chuck for releasably holding the first part with respect to the second part, the chuck comprising at least one radial opening in the second part, a tilt plate extending into the radial opening, the tilt plate including an aperture for receiving the first part and a radially extending finger received in said radial opening, the tilt plate aperture being defined by a surface having at least one edge, the tilt plate being moveable about a pivot point between a first, unlocked, position in which the first part is moveable with respect to the second part and a second, locked, position in which the edge contacts the first part to prevent at least one of axial movement and rotational movement of the first part relative to the second part; said pivot point being defined by said radial opening in said second part; and a tilt plate pusher engaging the tilt plate, the tilt plate pusher moving the tilt plate to at least one of its locked position and its unlocked position.

* * * * *